United States Patent
Truong (10) Patent No.: US 6,195,921 B1
(45) Date of Patent: Mar. 6, 2001

(54) VIRTUAL INTELLIGENCE SHOE WITH A PODIATRIC ANALYSIS SYSTEM

(75) Inventor: Vinncente Hoa Gia Truong, 2063 18th Ave., San Francisco, CA (US) 94116

(73) Assignee: Vinncente Hoa Gia Truong, San Jose, CA (US)

( * ) Notice: Subject to any disclaimer, the term of this patent is extended or adjusted under 35 U.S.C. 154(b) by 0 days.

(21) Appl. No.: 09/406,523

(22) Filed: Sep. 28, 1999

(51) Int. Cl.[7] .................................................. A43B 23/00
(52) U.S. Cl. ................................. 36/136; 36/1; 36/137; 73/172; 73/179; 600/592; 340/573.1
(58) Field of Search ................................ 36/132, 136, 88, 36/93, 140; 12/142 N, 146 M, 1 R; 73/179, 172; 600/592; 340/573.1

(56) References Cited

U.S. PATENT DOCUMENTS

| | | | |
|---|---|---|---|
| 5,033,291 | * | 7/1991 | Podoloff et al. ........................ 73/172 |
| 5,323,650 | * | 6/1994 | Fullen et al. ........................... 73/172 |
| 5,357,696 | * | 10/1994 | Gray et al. .............................. 36/136 |
| 5,408,873 | * | 4/1995 | Schmidt et al. ........................ 73/862 |
| 5,566,479 | * | 10/1996 | Gray et al. .............................. 36/137 |
| 5,642,096 | * | 6/1997 | Leyerer et al. ........................ 340/573 |
| 5,678,448 | * | 10/1997 | Fullen et al. ........................... 73/172 |
| 5,929,332 | * | 7/1999 | Brown .................................... 73/172 |
| 6,006,412 | * | 12/1999 | Bergmann et al. ............... 29/407.04 |

* cited by examiner

Primary Examiner—Paul T. Sewell
Assistant Examiner—Jila Mohandesi (57) ABSTRACT

The virtual intelligence shoe with a podiatric analysis system provided with a portable pair of shoe-like body types thereof, into two of which a miniature electronic module and an enclosed sensor mat are permanently embedded in the shoe-like with a mechanical air package enclosing the electronic module to serve as a shock absorption. A miniature electronic module comprises a transmitting circuit with pressure resistance, shoe temperature and warning buzzer for full memory capacity, which receives the variable pressure and temperature voltage signals, convert them into resistance (ohm) and Celsius, respectively. The electrical signals can be emitted in an infrared light signal. An enclosed sensor mat constitutes a thin, flexible, planar, resilient, and dielectric material that arrays seventy-four positions at strategic geometrical pattern to produce the precision of collecting data exerted by a foot or feet continuously and instantaneously in static and dynamic event during the full weight bearing in various activities. The conjunction of a pair of shoe-like body types, a digital foot scanner, a portable infrared light-receiving unit and a central integrator (servers) form a podiatric analysis system for enabling accurate information. An obtained information of each individual can be stored and analyzed for diagnostic means with respect to the foot or feet maladies. The virtual intelligence shoe with a podiatric analysis system is an unconventional, which can ultimately be used by anyone and capable to produce consistent foot or feet information to implement the changes in the foot or feet biomechanics by altering the shoes, orthoses or other modes. In a preferred form, a pair of shoe-like body types is virtually applied to any type of foot or feet maladies and worn daily as if they were conventional shoes under various terrain conditions.

7 Claims, 12 Drawing Sheets

VIRTUAL INTELLIGENCE SHOE WITH A PODIATRIC ANALYSIS SYSTEM

BACKGROUND OF THE INVENTION

1. Field of Invention

This invention relates generally to virtual intelligence shoe with a podiatric analysis system, which monitors the predetermined plurality of pressure regions underneath the foot or feet continuously and instantaneously at stance phases in various activities, and shoe temperature for diagnostic means that can virtually be applied to the alteration of orthoses, shoes and other modes at explicit foot or feet conditions.

2. Description of Prior Art

The shoe industry has existed for many years and rapidly evolved to multiple styles and functions of shoes to meet the population demand. Each pair of shoes has its own characteristic and purpose, which raises the question whether the same pair of shoes has a capability to deliver similar expectation in the next person. It is unlikely to anticipate that purpose because of the uniqueness of individual foot or feet mechanics when one engages full weight bearing in various activities. Feet are very complicated and very delicate organs, yet they do tremendous work. They make it possible for the human species to overcome the enormous forces of gravity, stand, walk, or run in an upright position with great efficiency. Each individual foot has a unique trait to coordinate the different mechanisms to properly achieve a functional alignment that allows the feet to reach optimal stability on the ground surface for human locomotion. It is not necessary to state that human species acquire shoes in order to walk or engage in other activities. The meaning of having a good pair of shoes is to increase the level of activities in individual expectation. Shoes can enhance the quality of life and most often can save lives of those suffering from diabetic diseases or peripheral neuropathy diseases and other foot maladies.

There are a number of devices, or shoes, which can monitor the forces and pressures underneath the foot or feet, but do not extend to the outdoor terrain. Each device has it own set of characteristics for collecting forces and pressures underneath the foot or feet because the complexity of foot biomechanics. For example, when the foot is getting ready to land on the ground surface, chances are those the greater degree of the internal rotation of lower limb in the flatfoot (pes planus) type and less in the high arch (cavus) type. This occurs differently in pathologic foot conditions. The internal rotation crosses the ankle joint, producing eversion of the subtalar joint, which in turn unlocks the transverse tarsal joint to produce a flexible forefoot and a flattening of the longitudinal arch. Concomitantly, the ankle is rapidly undergoing plantar flexion; the foot is flat on the ground. The initial impact of the foot against the ground is dependent on the limb velocity, acceleration and body weight. After the initial event, the foot is placed firmly on the ground with the heel relatively everted, a flexible transverse tarsal joint, and some flattening of the longitudinal arch. Once foot-flat has been achieved, there is increased vertical loading of the foot up to 120% to 300% of the body weight depending on the activity, and progressive dorsiflexion occurs at the ankle joint. At an appropriate gait cycle, the opposite limb passes the stance limb and the heel begins to rise off the ground. At this point, the vertical force decreases to 70%–90% of body weight depending upon the outcome of the particular activity.

The solution of collecting the forces and pressures underneath the foot or feet is very intricate and with multiple variables, thus, a set of data may vary depending on where the device or sensor placement, materials and other means due to the physics nature of compressive forces or pressures. As is known, there are numbers of load sensing devices useful for measuring and analyzing forces exerted on the feet. For example, U.S. Pat. No. 4,814,661, issued to Ratzlaff, et al., discloses systems for measurement and analysis of forces exerted during human locomotion. Systems including piezoelectric sensor elements advantageously mounted between supporting hard plastic material of various types or other mechanical similar materials. The sensor can further be supported by backup plate structures. Detachable mounting formed by mechanically interengaging parts allow transducer inserts to be made in a modular manner for use in different sensor shoes, thus allowing many more patients to be analyzed. Sensor shoe has a toe and heel. Shoe further has a medial and a lateral. Sensors are connected with small tubular wires to the desktop computer.

U.S. Pat. No. 5,269,081, issued to Gray, discloses a force-monitoring shoe for monitoring the force being applied to a patient's leg, as during walking. The device is contained within a shoe-like enclosure, which can be worn by a recuperating injured person. When force equal to a selectable value has been applied, an alert system notifies the patient. Another U.S. Pat. No. 5,357,696, issued to Gray et al., discloses a device for monitoring force being applied by a wearer thereof to the wearer's foot, as during walking. The device includes a pressure sensitive element that produces an electrical signal that is related to the force, with this signal being used to alert the wearer when a force more than a preselected value occur. Further, this signal can be used as input to data recording and analysis equipment. The signal transmission can be by direct wire connections, or via radio transmission.

U.S. Pat. No. 5,566,479, issued to Gray et al., discloses a shoe to be worn by diabetic persons, or persons afflicted with various types of foot maladies, where excess pressure exerted upon a portion of the foot tends to give rise to ulceration. The shoe body is fabricated to have relieved are as in the inner surface that contacts the foot at locations where the excess pressure is thought to possibly occur. When undesirable pressure occurs, there is an alarm unit to warn the wearer of the existence of this threshold. This warning alerts the wearer to remove the shoe to prevent the damage to the foot.

U.S. Pat. No. 5,642,096, issued to Leyerer et al., discloses a device for prevention of ulcers in the feet of diabetes patients. The device includes a sensor disposed in a contained liquid mass of a hydrocell carried in the shoe inner sole, the sensor being one that detects both pressure and temperature values to which the patient's feet are exposed. The outputs value of pressure and temperature are acquired by a warning signal generator to operate same to generate a patient discernible warning signal that indicates to the patient a need to take action to avoid continuance of exposure to the condition.

Further, there are devices that provide some form of measuring exerted force by the foot via a sensor mat between the insole and the foot. These devices include those described in U.S. Pat. No. 5,033,291 issued to Podoloff et al on Jul. 23, 1991, U.S. Pat. No. 5,323,650 issued to Fullen et al on Jun. 28, 1994, U.S. Pat. Nos. 5,408,873 and 5,678,448 issued to the present inventors on Apr. 25, 1995 and Oct. 21, 1997, respectively. These patents and certain others cited therein, deal with monitoring the force being applied to the foot to ascertain the general forces underneath the foot. Such force measurement devices are typically, externally exposed, heavy and cumbersome and, thus, act to restrict the wearer's ordinary movement and are intolerant to outfield environment. These sensor mats, which employ directly the sole of foot, tend to wrinkle, deform, unfit and slip away as a wearer attempts to step on it. As a result, they could produce erroneous information. Since the electronic package is exposed and dangling on the side of shoe with connector attached to sensor mat, it constrains the ordinary mobility of the user and is likely to lead to sudden failure. Another device for sensing ambulation force is U.S. Pat. No. 3,791,375 issued to Pfeifer on Feb. 12, 1974, where it is accomplished by a fluid-containing load that deflects and changes its volume in accordance with the amount of load thereon. This device is limited to the contact area, is heavy and bulky, which is disadvantageous and restricts the user from ordinary movement.

All of the above-cited patents have its own system or method of collecting data and interpreted within that particular process. They are ideal for laboratories and hospital clinics due to the cost of the unit and cumbersome for any ordinary user to access. In addition, there are no reference or control methods to collect those data, which can add incoherent and scatter information for any users to interpret. Thus, no virtual intelligence shoe arrangement exists, which is capable of producing accurate data by eliminating multiple factors related to pressures location and shoe temperature underneath the foot or feet continuously and instantaneously during the static and dynamic gait in various activities of a user thereof. Likewise, no attempts has been made, until now, to provide virtual intelligence shoe with a podiatric analysis system which will not only provide accurate data, but which can form part of a comprehensive record keeping in the central integrator (servers) and external pressures behavior underneath the foot or feet with a custom-made orthotic which is adapted, not only to the use of a particular individual, but also to the needs of diagnosing such as foot type and norm and abnormal pressures of all foot maladies.

In particular, there has been no attempt to provide a virtual intelligence shoe which has permanently embedded an electronic module capable communicating with a portable infrared light-receiving unit in order to take advantage of the fact that internet or personal computers are now in relatively widespread use as a convenient and accurate means of storing data, so as to integrate the virtual intelligence shoe with a podiatric analysis system into a comprehensive data keeping and diagnosing analysis system. Since the sensor mat is sandwiching in both upper and lower mid-soles that will give the virtual intelligence shoe with a podiatric analysis system with a sense of control reference to compare each individual over the general population as regards foot maladies.

SUMMARY OF INVENTION

It is a primary object of the present invention to provide a virtual intelligence shoe or shoe-like body types enclosure with a podiatric analysis system, referred to hereinafter generally as a shoe, with one or more outsole cavities and an enclosed sensor mat sandwiching in the upper and lower mid-sole layers containing a predetermined seventy-four-region and an electronic module, and a data acquisition transmitting circuit. The predetermined seventy-four-region sensors of a flexible sensor mat within the shoe comprises an independent shear stresses structure whereby pressures are directed primarily to those specific locations even when distributed unevenly within the shoe. The electronic module can monitor and store seventy-four-region sensors exerted by the foot or feet of a user continuously and instantaneously in static and dynamic event during the full weight bearing in various activities. The virtual intelligence shoe can be worn as if it were a conventional shoe or, other considerations are provided in an embodiment implemented for users with boots, sandal-like, and etc. This type of virtual intelligence shoe has been previously mentioned, which can be applied to the both shoes, right and left feet.

It is another object of the present invention to provide a shoe-like types with an enclosed predetermined seventy-four-region sensors of a flexible sensor mat and an electronic module permanently embedded in the outsole cavity space having a data acquisition transmitting circuit with pressure resistance, shoe temperature, circuit board temperature and warning buzzer when about saturated with memory capacity. A portable infrared light-receiving unit, disposed apart from said data acquisition transmitting circuit to facilitate the information in wireless means via remote telephone jack connection or personal computer.

It is a further object of the present invention to provide a shoe-like types with an enclosed predetermined seventy-four-region sensors of a flexible sensor mat and an electronic module permanently embedded in the outsole cavity space having a data acquisition transmitting circuit, in which the data can store in the electronic module or download to the central integrator by using a portable infrared light-receiving, unit. The data can be used as reference and determine the norm and abnormal pressures of all the users foot maladies.

The shoe-like body types having an enclosed predetermined seventy-four-region sensors of a flexible sensor mat and electronic module according to the present invention essentially comprises a custom-made orthotic, a shoe body, a mechanical air package or other mediums, a seventy-four region sensors of a flexible sensor mat, a temperature sensor, a buzzer, infrared transceiver, a replaceable 3.5 volts battery, a circuit board box, circuit board, and a data acquisition transmitting circuit.

The shoe-like type body in accordance with the present invention could be sports shoes, dressing shoes, boots, sandals and an ordinary shoe for children, adults, and shoe-like structure. Each shoe has an upper, custom-made orthotic (insole), two mid-sole layers and two outer soles. One of the outer soles has a receiving space, two-window medial (inside) border and back of heel area of the shoe. An electronic module, a mechanical air package, and a 3.5 volts battery are also housed in the outer sole.

In accordance with an embodiment of the present invention, an enclosed predetermined seventy-four-region sensors of a flexible sensor mat and an electronic module permanently embedded in the outer sole layer of shoe-like types is provided for measuring shoe temperature, circuit board temperature and pressures applied by the foot of a user via a custom-made orthotic, whereby predetermined seventy-four-region pressure sensors array are positioned to fit all size of users' foot in the shoe-like types.

In accordance with an additional embodiment of the present invention, the individual pressure region of sensors are arranged at predetermined location and permanently embedded sandwiching in the mid-sole layers to serve as the reference pressure areas and wrinkle free. This gives the data the magnitude of vertical force rather than shear stresses as other devices.

BRIEF DESCRIPTION OF DRAWINGS

The foregoing and other features and advantages of the present invention will be clearly rationalized from the following detailed description and the accompanying drawings, in which.

DETAILED DESCRIPTION OF PREFERED EMBODIMENT

Figure 1:
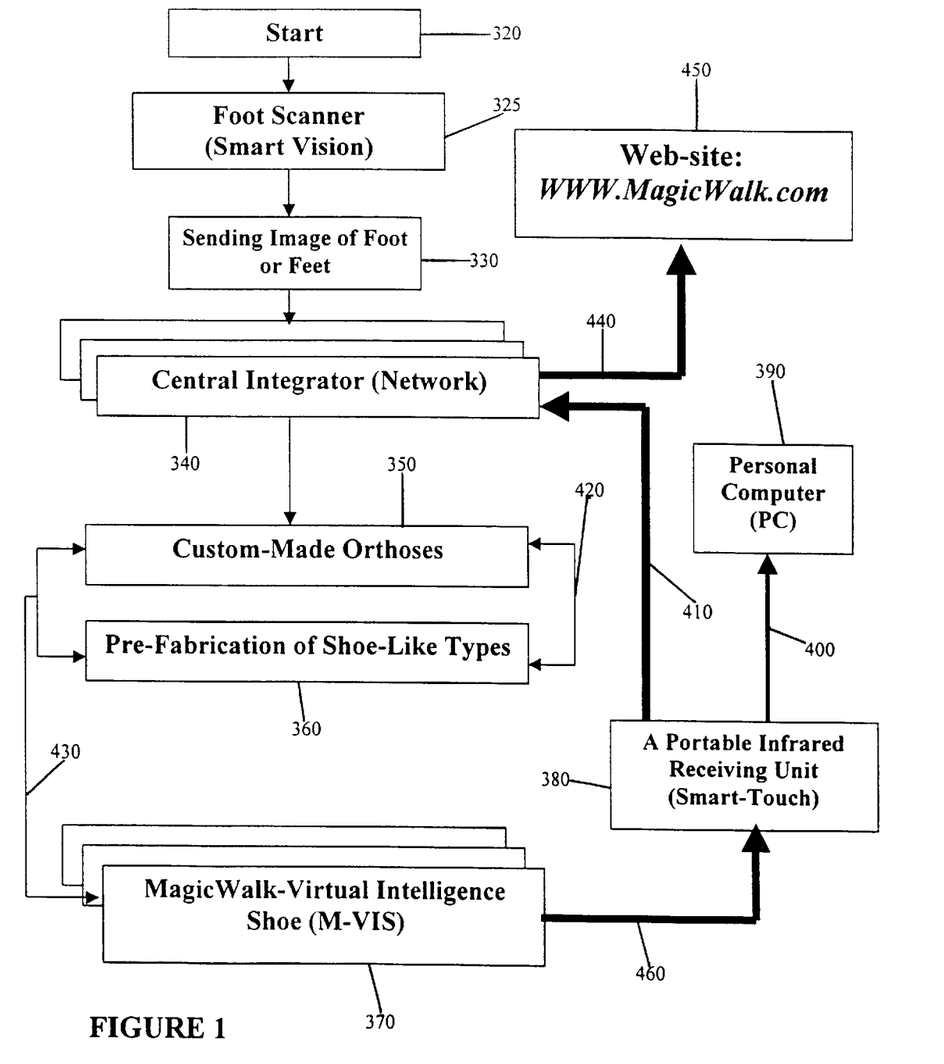
FIG. 1 is a flow chart representation of the virtual intelligence with a podiatric analysis system of the present invention.

Referring to FIG. 1 shows a flow chart of a podiatric analysis system of the present invention and others are currently developing, the start system 320, and a foot scanner 325 sends the images of the foot or feet 330 to the central integrator (servers) 340. The images can be processed and developed the custom-made orthoses 350 for that particular individual. The pre-fabrication shoes 360 and custom-made orthoses assemble in such a way that meet the individual foot or feet characteristics. The assembled shoe 420 converts 430 into more a computer shoe and called a virtual intelligence shoe 370, which can be ready to use by any individual. The virtual intelligence shoe 370 can store the data up to many operational hours and be able to transfer information to a portable infrared light-receiving unit 380. Moreover, a portable infrared light-receiving unit 380 has a capability to store information as much as the virtual intelligence shoe 370. The information can deliver 400 to the remote personal computer or 410 to the central integrator (servers) for analytical process in simultaneously and instantaneously. The analysis information can be sent directly 440 to the user by posting at the web-site services 450 or mailing.

Figure 2:
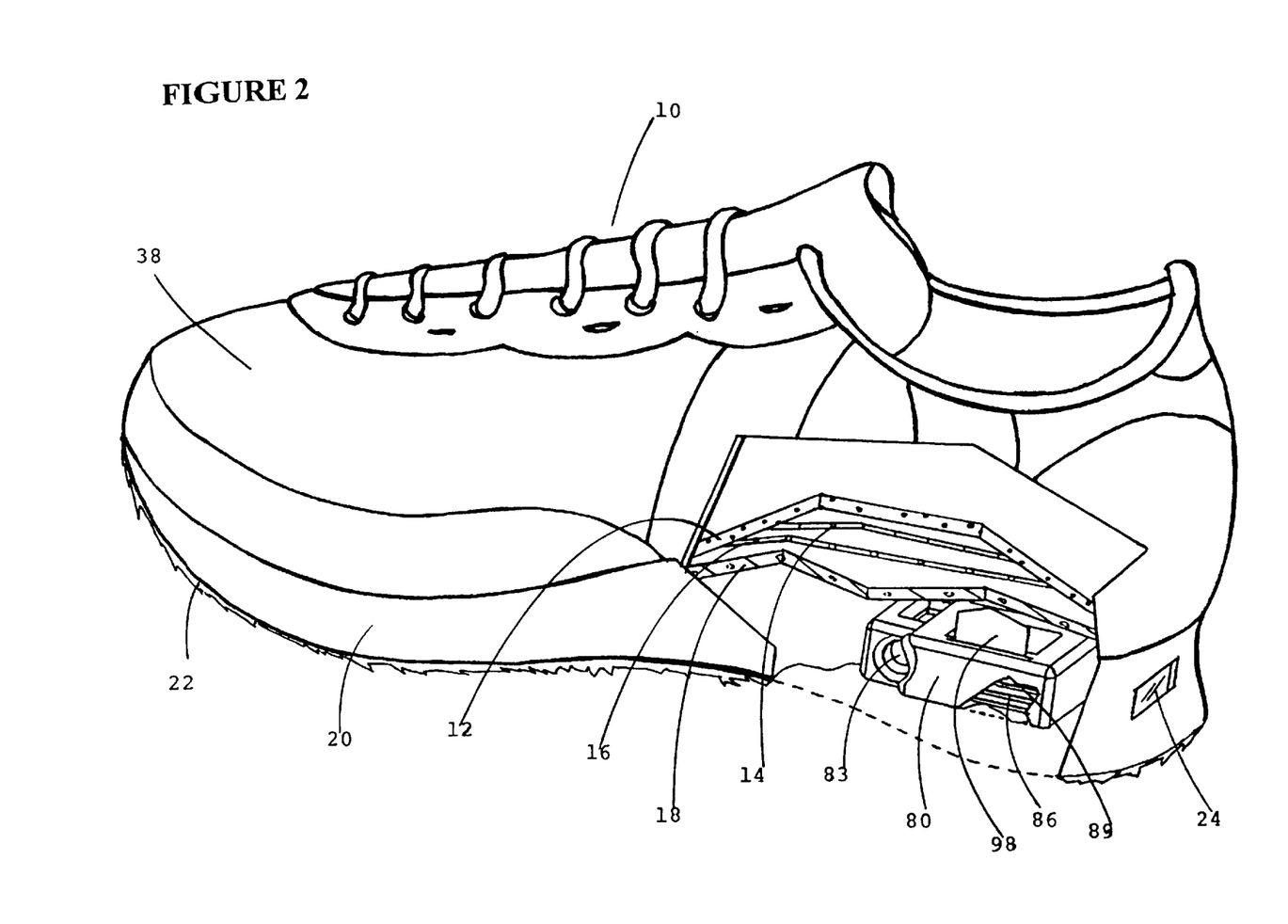
FIG. 2 is a schematic depicting a conventional shoe of the present invention, partially cut away, according to the objects of the present invention.
Figure 3:
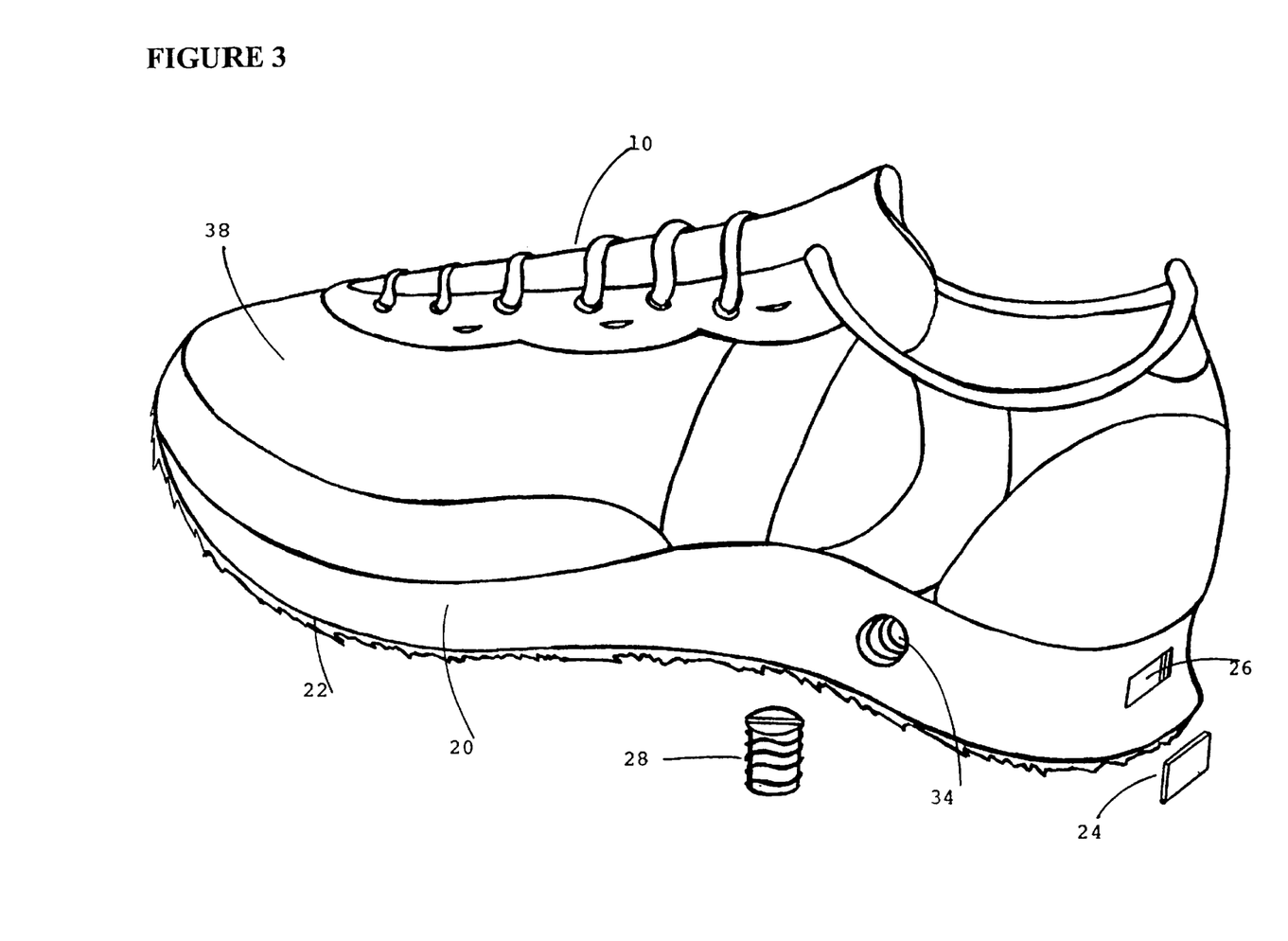
FIG. 3 is a schematic depicting a conventional shoe of the present invention according to the objects of the present invention.
Figure 4:
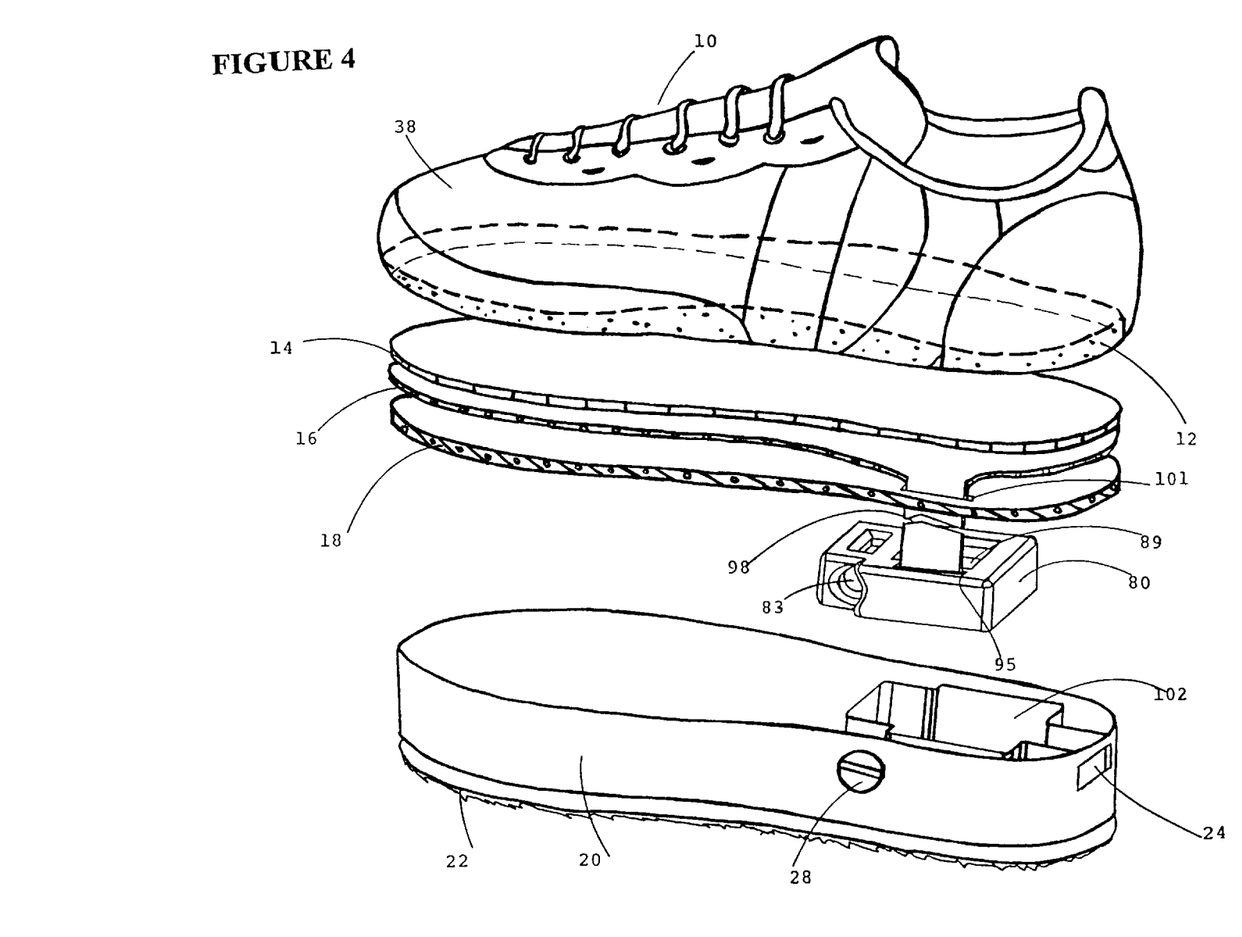
FIG. 4 is a schematic exploded view of a preferred embodiment of the present invention.

Referring to FIGS. 1, 2, and 3 the conventional shoe with a miniature electronic module and an enclosed sensor mat according to the first preferred embodiment of the present invention essentially comprises a shoe body 10, an upper 38, a custom-made orthotic 12, an upper mid-sole layer 14, a lower mid-sole layer 18, a flexible sensor mat 16, a mechanical air package 80, a threaded plastic bolt 28, a clear plastic rectangle window 24, and a 3.5 volts battery 2.

The shoe body 10 has an upper 38, a custom-made orthotic 12, two outer soles 20 and 22 of a wear resistant and dielectric material. The flexible sensor mat 16, upper mid-sole 14, lower mid-sole 18, mechanical air package 80, 3.5 volts battery entrance 83, a threaded cavity 34, a window 26, and data acquisition transmitting circuit are all disposed in a receiving cavity 102 in the outer sole 20.

In the first preferred embodiment, the flexible sensor mat 16 is connected to a circuit board 86, which has a tail end 98 piercing through two slits 101, and 95 of the lower mid-sole 18 and the mechanical air package 80, respectively. The tail end 98 accommodates the height of the any type of outer sole by trimming the lengthwise and reconnects the conductive leads 160 with solder paste. In addition, the mechanical air package 80 places in the receiving cavity 102 to insulate the miniature electronic module from extreme vibration during the various loads of human activities and serves as shock absorption. The outer sole 20 includes a clear plastic rectangle window 24 for emitting the data via infrared light and a threaded plastic bolt 28 for replaceable battery. A clear plastic rectangle window 24 and a threaded plastic bolt 28 are sealed tightly with a special adhesive material to prevent moisture and dirt to enter the receiving cavity 102. The outer sole 22 is specially made dielectric material to prevent the electrical static from ground and permits a user to access to a sensitive environment or other terrain.

Figure 5:
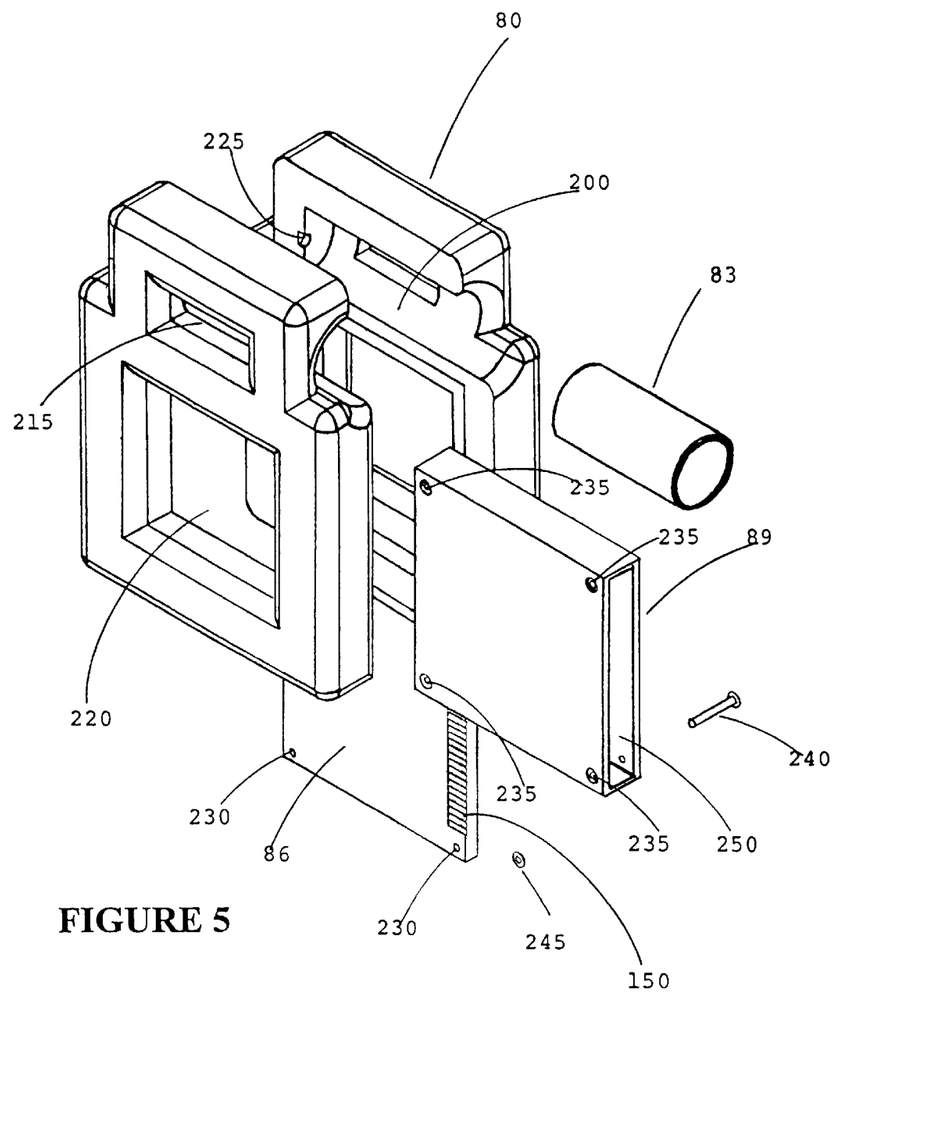
FIG. 5 is a schematic exploded view of a preferred embodiment of FIG. 4.

Referring to FIG. 5 shows an exploded view of a first preferred embodiment, the mechanical air package 80 houses the 3.5 volts battery, circuit board box 89 and circuit board 86 with an upper window space 215 and a bottom window space 220 for lightness and shock absorption. A 3.5 volts battery has a receiving space 200 and an electrode end 80 in the mechanical air package 80. A circuit board 86 comprises of four holes 230 periphery with finger-like projection conductive leads 150 to invite the connection from bottom layout tail end 153. The circuit board box 89 has four through-and-through holes 235 to match the screws 240 and nuts 245 with an opening space 250 to insert the circuit board 86.

Figure 6:
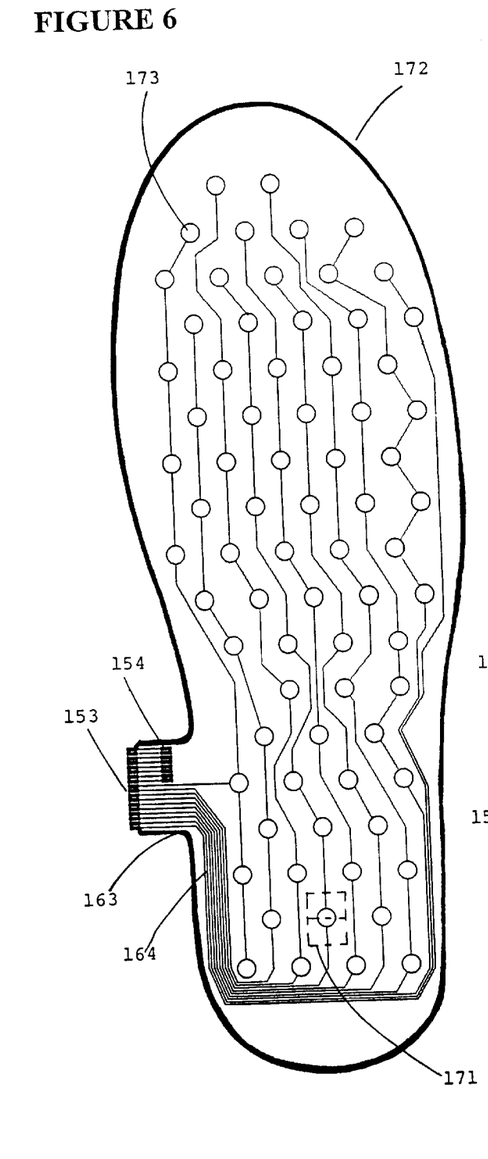
FIG. 6 is a detailed schematic illustrating conductive traces and sensor regions on a bottom surface of the bottom substrate of FIGS. 4 and 5.
Figure 7:
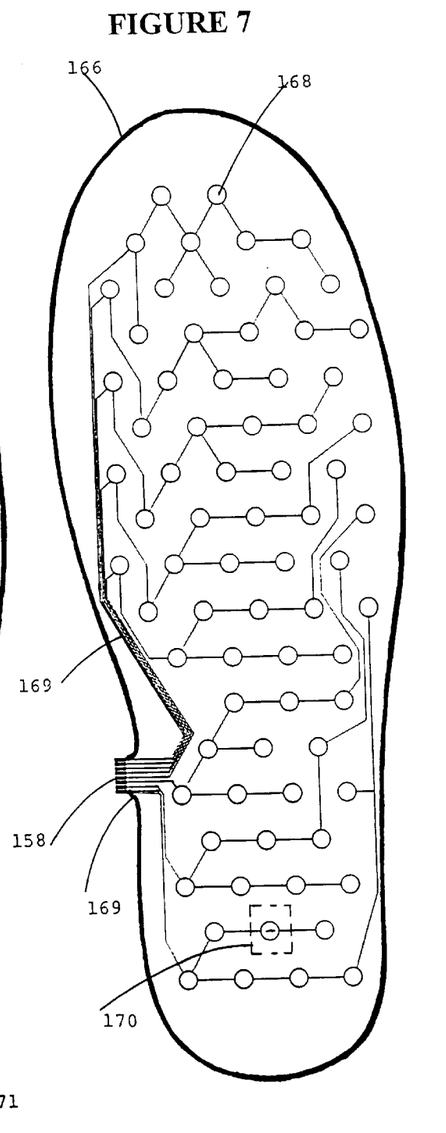
FIG. 7 is a detailed schematic illustrating conductive traces and sensor regions on a top surface of the top substrate of FIGS. 4 and 5.
Figures 8, 9:
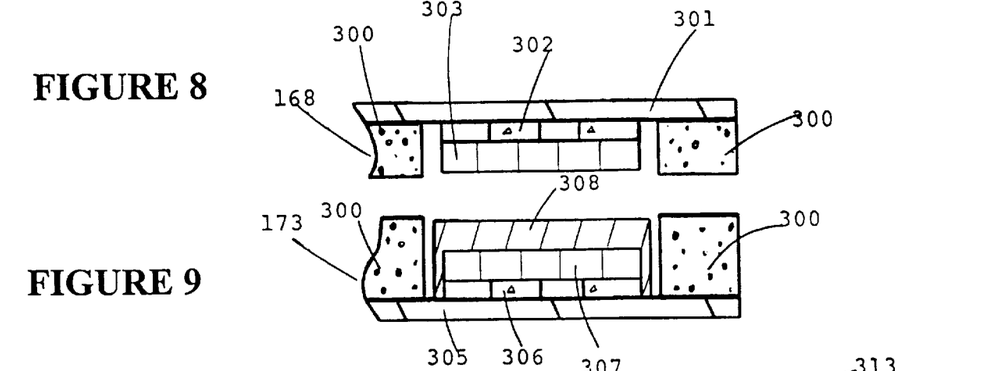
FIG. 8 is a detailed schematic of a portion of the sensor region illustrating the cross-sectional view of planar arrangement of the top sensor mat of FIGS. 4, 5 and 6.
FIG. 9 is a detailed schematic of a portion of the sensor region illustrating the cross-sectional view of planar arrangement of the bottom sensor mat of FIGS. 4, 5 and 6.
Figure 10:
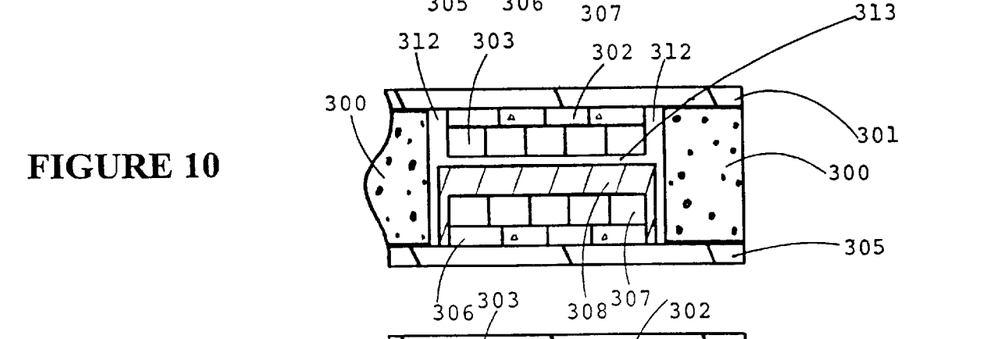
FIG. 10 is a detailed schematic of a portion of the sensor region illustrating the cross-sectional view of planar arrangement of the non-conductive sensor mat of FIGS. 4, 5 and 6.
Figure 11:
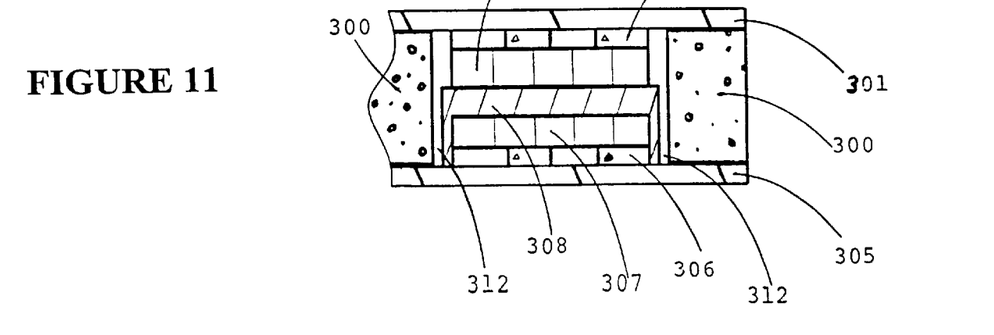
FIG. 11 is a detailed schematic of a portion of the sensor region illustrating the cross-sectional view of planar arrangement of the conductive sensor mat of FIGS. 4, 5 and 6.

FIGS. 6 and 7 are shown generally the configuration of a seventy-four-region sensors 168 distribution constructed in a first preferred embodiment. The seventy-four-region sensors 168 of an upper layout 166 and a bottom layout 172 represent the rows and columns, respectively. The rows and columns of both upper layout 166 and bottom layout 172 are typically missing none to few sensor regions due to the intricate geometrical pattern of the foot. Each sensor region 168 has target a critical loading pressure via various loads of human foot at stance phases and able to extend horizontally and vertically to fit all foot sizes with a circle shape. The seventy-four-region sensors 168 supported by flexible Kapton backing sheets from Rogers Corp., which made of superior adhesion, dynamic flexibility, low and predictable dimensional change, resistance to harsh processing chemicals and inherent flame retardant performance. The backing sheet should be made of a dielectric material. The configuration of seventy-four-region sensors 168 of the upper layout 166 and the bottom layout 172 are coincidentally sandwiching that matched the configuration and separated 313 by a pressure variable resistor ink 118-44 from Creative Material Corporation.

Each of the row and column sensor regions has conductive traces that is connected to its corresponding sensor region and which extend on along the tail end pathways 169 and 163 of the upper layout 166 and bottom layout 172, respectively. FIGS. 8, 9, 10, and 11 show cross-section of enlarging sensor regions 170 and 171. The endmost layers 301 and 305 designate the physical support and backing layer for other layers to deposit their materials. In a preferred embodiment, the Kapton backing sheet may have a thickness of 0.001" followed the etching, sputter coating, and other processes. The deposited layers on the backing layer includes the copper layers 302 and 306, conductive ink 112–115 layers 303 and 307 and adhesive layer 300 of the upper layout 166 and bottom layout 172, respectively. The deposition process of conductive ink 112–115 layers 303 and 307 is extremely vulnerable to high heat and best result when cured for 3 to 5 minutes at a constant temperature 106.5 C. Similarly, the pressure variable resistant ink layer 308 has to be deposited and cured on the bottom layout 172 with a slightly larger dimension than the conductive ink layer 306 preventing conductive inks touching each other. The nature of the pressure variable resistant ink is extremely sensitive with heat and thickness, which responds the pressure loads at wide range of spectrum and generally thicker than conductive ink layers 303 and 307. The thickness of the pressure variable resistant ink layer 308 of the sensor region 173 was used 0.002" to produce a resistance of less than two M ohms. The deposition of adhesive layer 300 should have 0.1" circumferencially 312 the sensor region 168 and 173 to relief the mechanical loading during the static and dynamic activity of human foot or feet.

Figure 12:
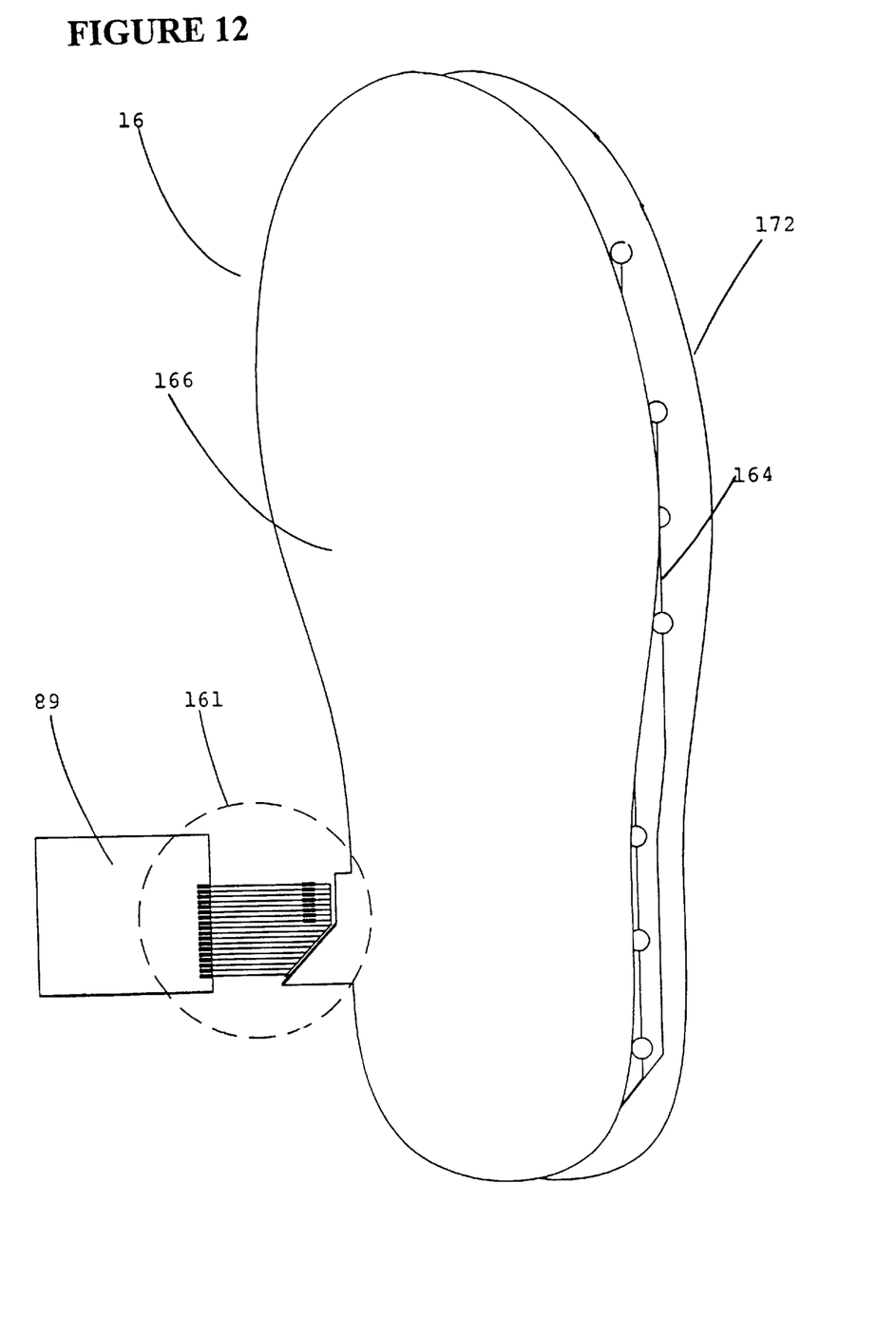
FIG. 12 is a schematic top view of a sensor mat with extension conductive traces and an electronic module of preferred embodiment of the FIG. 4.
Figure 13:
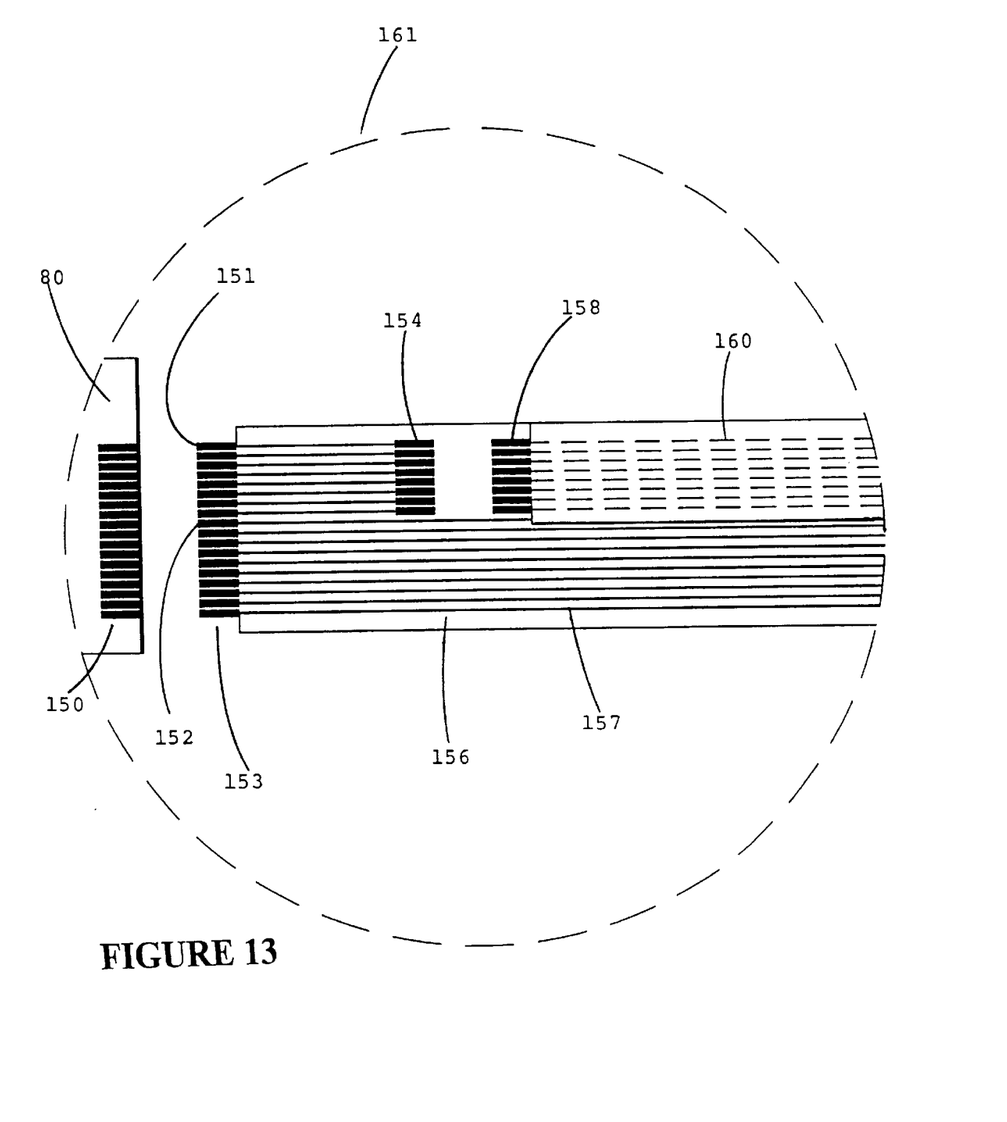
FIG. 13 is an exploded top view of extension conductive traces with interconnected a miniature electronic module of preferred embodiment of the FIG. 12.

Referring to FIGS. 12 and 13 show the enlarge portion of tail ends 158 and 153. A standard print circuit board 89 connects to the tail end 153 of the flexible sensor mat 16, together with conductive leads 157 and 160 to form contacts arranged to coincide with contact seventy-four-region sensors 168 by conductive traces layers 166 and 172. The primary finger-like projection 151 represents the number of rows, begins row 0, and ends with row 7; the secondary finger-like projection 152 represents the number of columns, begins column 0, and ends with column 9. The tail ends 158 and 153 connect to 154 and 150 by soldering, which reduce the cost, eliminate the bulkiness, and lessen the electrical noises. This method will bypass the fasten connector.

Figure 14A:
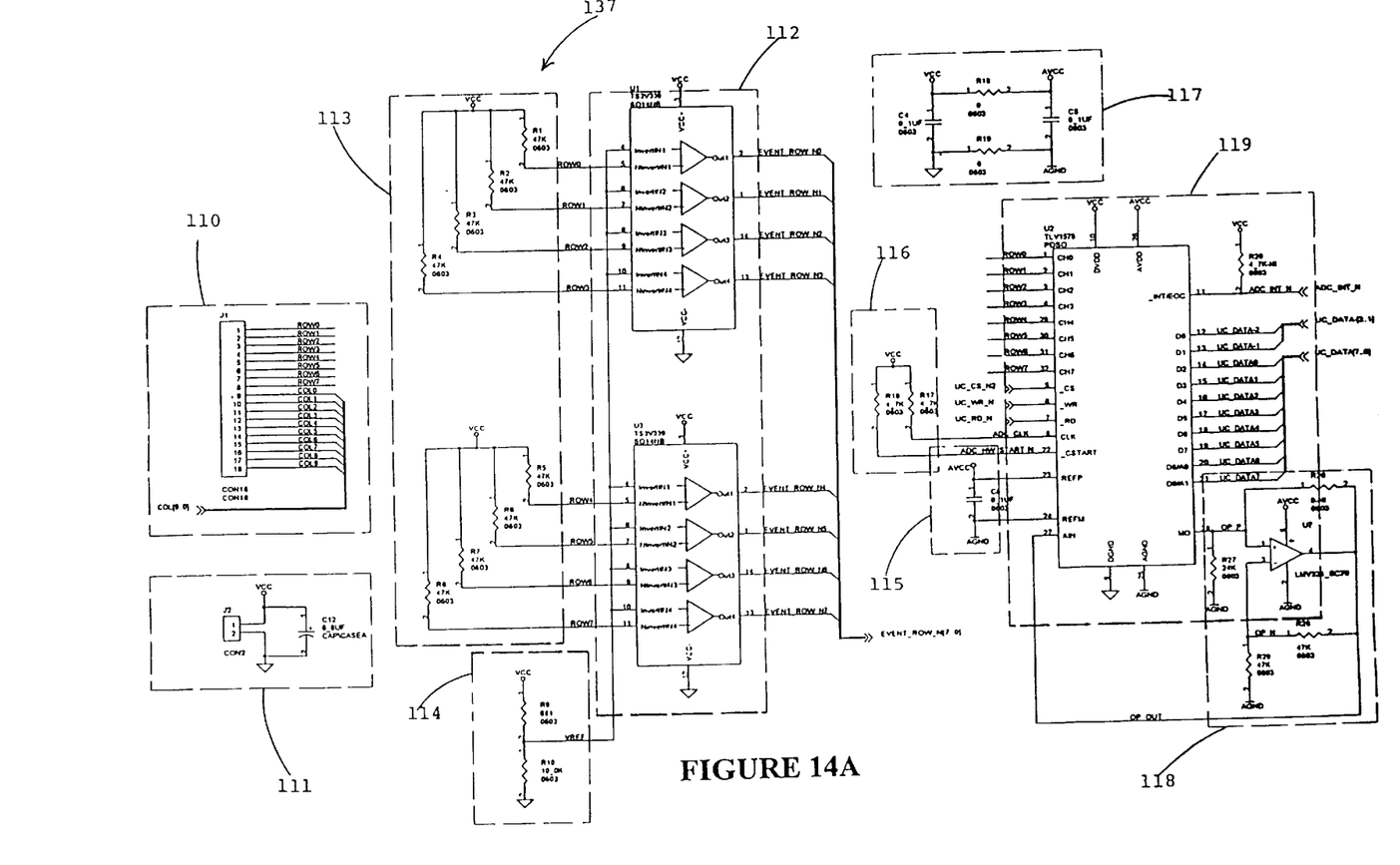
FIGS. 14A, 14B and 14C illustrate a circuit diagram and components' model of a data acquisition transmitting circuit of the present invention.
Figure 14B:
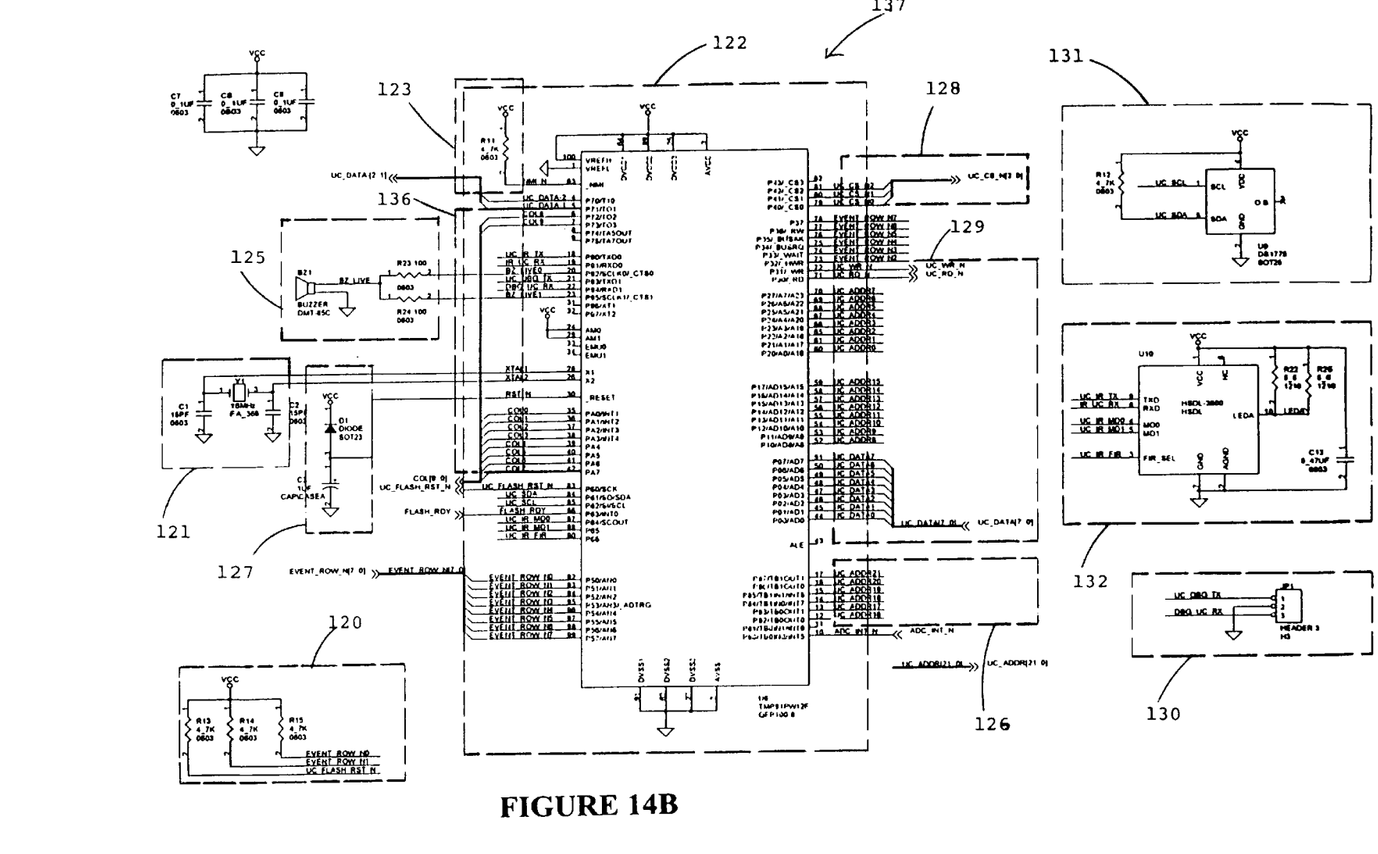
Figure 14C:
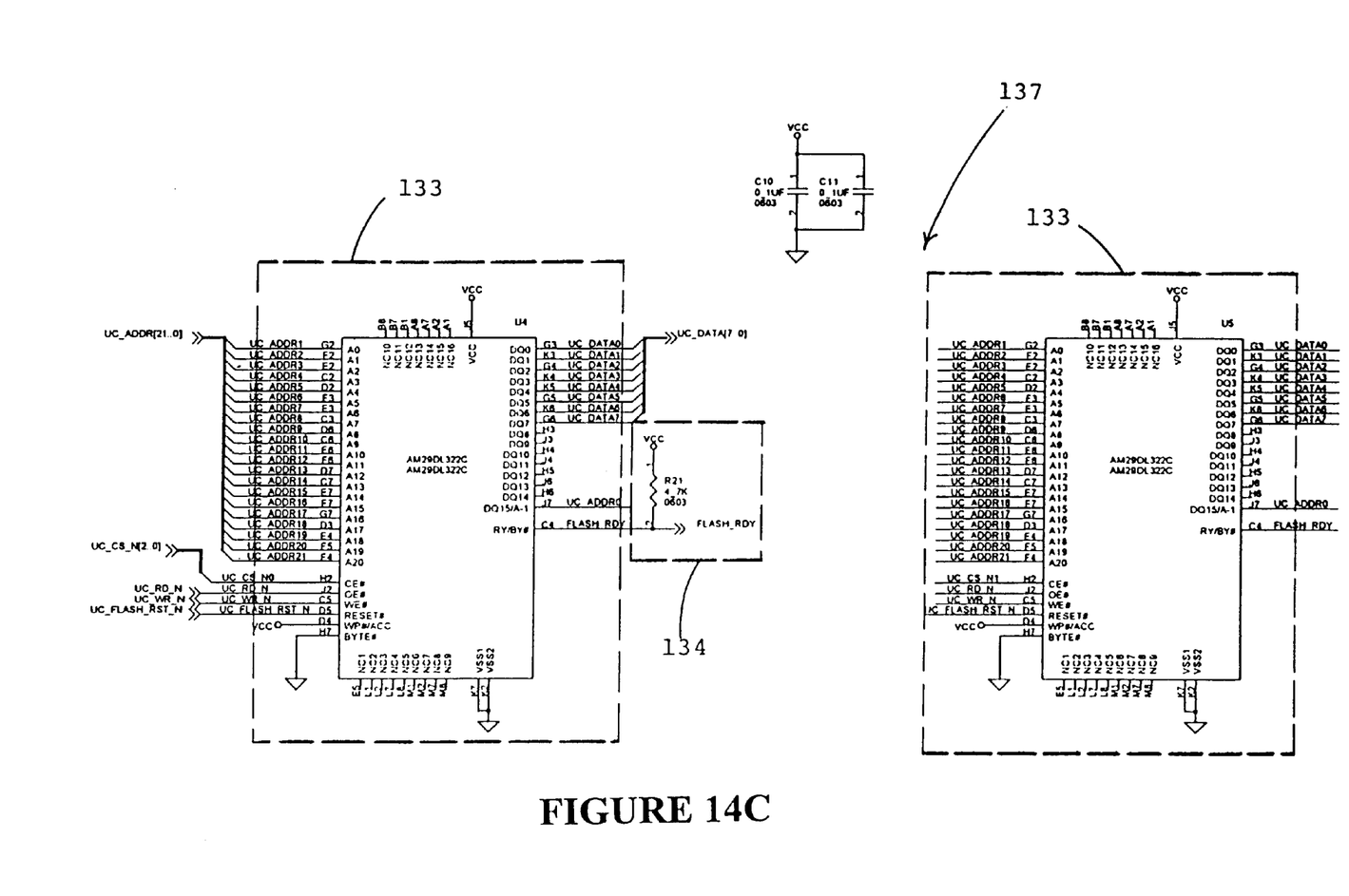

Referring to FIGS. 14A, 14B and 14C, the data acquisition transmitting circuit 137 of the present invention includes a circuit board 86 and a flexible sensor mat 16. The seventy-four-region sensors of the flexible sensor mat 16 are arranged in 8 rows and 10 columns 110. Each column registers at a time, which leaves other sensor region columns with one side open that allows the Analog to Digital converter 119 having the computation. In the computation of each sensor region can be transformed its resistance according to the changes of variable pressures via the human foot or feet activities. The pull-up resistors are using in a voltage divider 113 to create an individual sensor region in a given column. The pull-up resistors are known value in 113, which measures the resistance of the sensor regions by measuring voltage in a voltage divider 113 using the Analog to Digital converter 119. This will allows the eight channels or rows to be converted at the same time.

Giving the fact that the sole of foot or feet has a moment of weight bearing and non-weight bearing throughout the stance phases of human activities and called its an event. The time of the foot or feet actual hit on the ground varies from one individual to the next, even in the same person at various activities. The voltage comparator bank of the models 112 was used to capture start and stop time of the events with 0.1 ms accuracy for seventy-four-region sensors. The use of comparators of the models 112 can access the events quickly and efficiently of whether there was an event or not. The voltage references of comparators 114 approach the coming voltage of each column of the sensor regions by comparing to a known value in a voltage divider 113. When an event occurs, a voltage crosses the threshold imposed by the voltage reference of comparators 114 and toggles the output of the comparators.

In the analog buffer of the models in 118, an Operational Amplifier (OP) was used in a one-gain of non-inverting high input impedance configuration. As in an 8 rows and 10 columns of a flexible sensor mat 16 output current is low than the Analog to Digital converter 119 switches into the capacitors type. In order to have a proper measurement, it would be required a higher sampling time. The task of the analog buffer 118 is to provide sufficient current for the input of the Analog to Digital converter 119 ensuring the internal capacitors of the converter, which charges properly during the minimum sampling time.

The decoupling capacitors and segmentation resistors 117 are essential for localized high frequency of decoupling capacitors to provide in each critical component and assist to keep apart from analog and digital supply planes avoiding the sharing current. This would degrade the analog section of the circuit from the ground and supply noises. The segmentation resistors 117 further assist to preserve the net names during the Printed Circuit Board layout for analog and digital supplies, which can ease these separation tasks. Moreover, the decoupling of Analog to Digital reference voltage 115 improves noise rejection from the Analog to Digital converter 119.

The circuitry of the first preferred embodiment of an electric source 111, a digital temperature sensor 131, a micro-controller crystal oscillator 121, a micro-controller reset 127 and a buzzer 125 display in FIGS. 14A and 14B. The manufacturers recommended for the corresponding circuit connectivity have determined each circuit. For instance, the micro-controller reset circuit 127 provides a reset to the micro-controller 122 of having power-on for ensuring the proper initial statement. The NMI interrupt 123 uses to set the disable condition of power at initial statement by the pull-up resistors. The buzzer circuit 125 uses to alarm a user when memory is about to saturate and ready to download the information in an appropriate site. A digital temperature sensor circuit 131 is utilized of monitoring the temperature condition of the shoe and circuit board 86.

The micro-controller 122 is the core of reading from the Analog to Digital converter 119, comparators 112 and temperature sensor 131, which furthers the communications with infrared transceiver 132 and debug serial port connector 130. The micro-controller circuit 122 includes a programmable chip 128 and memory mapped extensions of Address/Data and Read/Write signals 129. In a programmable chip 128 allows to activate these signals when a given range of memory is assessing, which serves a reasonable amount of selection interface to the flash memories 133 and Analog to Digital converter 119. The lines 126 use as an extension of address bus to access the full range of flash memories 133; the column selection port 136 uses to address one column of the sensor regions at a time. It is typically one of the pins driving low and the remainder set uses the high impedance (inputs) from scanning fashion until all the columns of the sensor regions are completely addressed. The captured data can save in an encoded space saving format of the flash memories 133 and each flash memory has a capacity from 1 MB to 4 MB, which bring a total of 1 MB to 8 MB. The interrupt line 134 from one of the flash memories 133 can be used by the micro-controller 122 to detect whenever the consuming operations are finished. The pull-up resistor uses as an output open collector and shares between two flash memories 133.

The micro-controller 122 processes the frequency signal received to obtain a value, which includes a pressure value or values obtained by the seventy-four-sensor sensor region of the flexible sensor mat 16, the temperature sensor 131 of the shoe and PCB, power-down mode when sensor regions are inactive, and register the starting time, date of event and specific location of the sensor regions. The information can be transmitted via infrared transceiver 132 and debug serial port connector 130 by serial asynchronous interfaces.

Accordingly, the reader will see that the virtual intelligence shoe 370 with a podiatric analysis system of this invention can be able to constant monitoring the pressure underneath the foot or feet at specific location in multiple steps of the user when engaged at full weight bearing in various activities. It is more accurate and versatile than any mere shoe could be, while being simple and easy to use with the cost of less than expensive pair of shoes. In use, the flexible sensor mat 16 and a miniature electronic module are permanently placed within an outer sole of the shoe 10. The pressure measurement of the seventy-four-region sensors is capable of measuring the instantaneous resistance during various activities of the human foot or feet. The plantar or sole of the foot has a relative velocity of less than 2 seconds to complete the cycle from heel to toe during the gait. The scan rate was used 0.1 ms, which was more than sufficient to capture the significant instantaneous pressure resistance value. At the same time, the shoe and circuit board temperature can be taken at 10 to 30 minute time intervals to assure the quality of the virtual intelligence shoe 370. The virtual intelligence shoe 370 has only a finite life, the design by which the circuit board and components enable the life of a miniature electronic module to extend beyond that of the original shoe. A buzzer was also installed to use as warning the user the memory is about to saturate and ready to transfer that information via a portable infrared-receiving unit 380.

Additionally, the virtual intelligence shoe 370 has the shoe body 10 that makes up multiple layers as such a custom-made orthotic 12 to provide one of the precursors through the analytical process. The sensor regions have an intricate pattern distribution in such a way that fit all the sole of the foot sizes and wrinkle free at the critical biomechanics of loading areas during the full-weight bearing activities, which able to obtain the information of individual foot accurately. The received information from the user that can be computed in velocity, acceleration, frequency of steps, pressures, forces, time, date and other means. Thus, the virtual intelligence shoe 370 will be available for the user at a low cost, which will be able to increase the number users that convert the data at a massive population rate. The massive information can be compared historical value to determine the norm and abnormal external biomechanics pressure of the human foot or feet during the static and dynamic at various activities. The user can take advantage of the virtual intelligence shoe 370 by accessing the web-site services for diagnostic means and comprehensive treatment for those particular user foot modalities. Anyone and anywhere can use the virtual intelligence shoe 370 with a podiatric analysis system, which enhances the possibility for clinicians to diagnosis and treatment through the network services. It is helpful to monitor constantly for those suffering diabetic diseases and other neuromuscular diseases because they have unpredictable stages of bone degeneration. It will alarm the clinicians to implement an appropriate treatment protocol for that particular individual.

Although the description above contains many specificities, these should not be construed as limiting the scope of the invention but as merely providing illustrations of some of the presently preferred embodiments of the this invention. For example, the electronic module can have physical sizes that can be securely fitted in the orthotic; the circuit board can have other shapes, such as trapezoid, circular, oval, hexagon, etc. A virtual intelligence shoe 370 has a right and left shoe.

Thus, the scope of the invention should be determined by the appended claims and their legal equivalents, rather than by the examples given.

What is claimed is:

1. A virtual intelligence shoe with a podiatric analysis system, which is stored entirely in the outsole without directly contacting the foot and can be worn daily as if it were a conventional shoe, can be monitored and stores a plurality of predetermined pressure points instantaneously and continuously when a user engages in static and dynamic events during the full weight bearing in various activities at different terrain conditions, said virtual intelligence shoe comprising:

(a) a virtual intelligence shoe body, said shoe body having an upper, a custom-made orthotic, lower and upper mid-sole layers, a round compartment which houses a 3.5 volts battery from which an old battery can be removed and a new battery can be inserted, a transparent or semi-transparent window in the outsole through which infrared light can be transmitted or received, said outsole having a cavity space;

(b) a mechanical air package, disposed in said cavity space of said outsole, and being filled with air or other shock-absorption materials;

(c) a battery power source, disposed in said mechanical package or other shock-absorption materials of said outsole, and being replaced when power runs out;

(d) a flexible sensor mat positioned between two layers of outsole and from which voltage signals are generated and said voltage is based upon and varies with, the amount of pressure from the foot;

(e) a miniature electrical module, disposed in said mechanical air package of said outsole, obtaining and storing primary information of the foot or feet biomechanics and temperature sensor signals from said flexible sensor mat and shoe temperature;

(f) a data acquisition transmitting circuit, disposed in said cavity space of said outsole, and a infrared light transmitting circuit, said data acquisition transmitting circuit computing said frequency signal to obtain variable values, which is modulated by said infrared transmitting circuit prior to being emitted.

2. A virtual intelligence shoe with the podiatric analysis system of claim 1, wherein said primary information of the foot or feet biomechanics analysis means is adapted for permanent embedding in the cavity space of said outsole.

3. A virtual intelligence shoe with a podiatric analysis system of claim 1, wherein said the primary information of the foot or feet biomechanics means comprising:

(a) a flexible sensor mat positioned between the upper and lower sections of the outsole with predetermined seventy-four-region sensors arranging to accommodate the foot sizes and foot biomechanics;

(b) a temperature sensor for monitoring the shoe temperature and circuit board;

(c) an electronic module means for executing instructions controlling said scanning flexible sensor mat circuitry, power saving circuitry and for processing said information indicative of various resistance responding to the various loading of the foot or feet biomechanics by said predetermined seventy-four-region sensors and shoe temperature, circuit board temperature, and said storing information multitude of hours with warning buzzer whereabouts saturated memory capacity;

(d) a wireless portable infrared light receiver means for coupling said an electronic module means at suitable distant to a central integrator (servers) means or a remotely computer to enable the transfer primary or selected information of the foot or feet biomechanics, between said electronic module means and said central integrator (servers) means or personal computer;

(e) central integrator (servers) means coupled to said images of the foot or feet and information of foot or feet biomechanics in said wireless portable infrared light receiver means to a network of said multiple executed programs for data analysis and storage and said end user access to the web-site services.

4. A virtual intelligence shoe with a podiatric analysis system of claim 1, wherein said flexible sensor mat includes:

(a) a scanning circuit further comprising electrical conductive type, said upper and bottom layout electrode sheets being vertically coincident individual region sensor electrodes, said plurality individual region sensor electrodes being connected and electrically bundled to form conductive trace that follow a directly terminal path;

(b) pressure variable resistor inks applied directly on the region electrodes at least one of the sheets with a variable thickness responding to various loading trials;

(c) an adhesive layer applied to at least one of the region electrode sheets in said areas between the electrode regions to secure the upper and bottom sheets from sliding in said facing relationship.

5. A virtual intelligence shoe with a podiatric analysis system of claim 1, wherein said individual region sensor electrodes are geometrically pattern to respond in various foot types, sizes and biomechanics by increasing or decreasing the length of each sensor region electrode vertically and horizontally.

6. A virtual intelligence shoe with a podiatric analysis system of claim 1, wherein said flexible sensor mat sandwiching the upper and lower mid-sole layers to protect the sensors from wrinkling or protecting the sensors from being subjected to shear stresses.

7. A virtual intelligence shoe with a podiatric analysis system of claim 3, wherein said information means being stored and analyzed in data acquisition transmitting circuit located in the outsole.

* * * * *